(12) United States Patent
Sogaro (10) Patent No.: US 8,950,966 B2
(45) Date of Patent: Feb. 10, 2015

(54) APPARATUS FOR DISCHARGING A POURABLE SUBSTANCE

(75) Inventor: Alberto C. Sogaro, Kronberg (DE)

(73) Assignee: Sulzer Mixpac AG (CH)

( * ) Notice: Subject to any disclaimer, the term of this patent is extended or adjusted under 35 U.S.C. 154(b) by 1174 days.

(21) Appl. No.: 12/664,849

(22) PCT Filed: Jun. 19, 2008

(86) PCT No.: PCT/DE2008/001022
§ 371 (c)(1),
(2), (4) Date: Jun. 9, 2010

(87) PCT Pub. No.: WO2008/154912
PCT Pub. Date: Dec. 24, 2008

(65) Prior Publication Data
US 2010/0239355 A1 Sep. 23, 2010

(30) Foreign Application Priority Data
Jun. 20, 2007 (DE) .................... 20 2007 008 646 U (51) Int. Cl.
*B05C 17/00* (2006.01)
*A61M 5/28* (2006.01)
(Continued)

(52) U.S. Cl.
CPC ............... *A61M 5/285* (2013.01); *A45D 33/00* (2013.01); *A61M 5/282* (2013.01); *A61M 35/003* (2013.01); *B65D 47/205* (2013.01); *A61M 2039/229* (2013.01)
USPC ............................ 401/208; 401/183; 401/263

(58) Field of Classification Search
USPC ......... 401/128, 280, 281, 292, 107, 108, 116, 401/134, 135, 143, 261, 263, 264, 401/183–186; 251/215, 216; 222/209, 213
See application file for complete search history.

(56) References Cited

U.S. PATENT DOCUMENTS 279,418 A * 6/1883 Newton ......................... 251/216
3,157,323 A * 11/1964 Kitterman ..................... 222/520
(Continued)

FOREIGN PATENT DOCUMENTS

DE 1441390 11/1968
DE 69922033 4/2000
(Continued)

OTHER PUBLICATIONS

International Search Report as mailed on Nov. 27, 2008 for International Patent Application PCT/DE2008/001022.
(Continued)

*Primary Examiner* — David Walczak
*Assistant Examiner* — Bradley Oliver
(74) *Attorney, Agent, or Firm* — Quarles & Brady LLP (57) ABSTRACT

Proposed is a device for applying a flowable substance comprising an outer shell (14) forming a receptacle for the flowable substance, as well as at least one portionally cylindrical insert (12) assigned to an application tip (22) and open at one end and closed at the other end and its shell featuring at least one orifice (34) connected to the open end. The outer shell (14) is shiftable in relation to the insert (12) between a blocked position in which a fluid flow between the outer shell (14) and the insert (12) is blocked by means of a sealing device and an activated position in which the fluid flow between the outer shell (14) and the insert (12) is released. The insert (12) has a male screw thread (20) mating the outer shell (14), the flowable substance flowing after twisting of the insert (12) in relation to the outer shell (14) and release of the orifice (34) into the insert (12). The outer shell is made, at least portionally, of an elastomeric plastics material. The insert (12) comprises a collar ring acting as a stop for the insert (12) at the outer shell (14) and as an actuator for shifting the outer shell (14) in relation to the insert (12).

13 Claims, 7 Drawing Sheets (51) Int. Cl.
*A45D 33/00* (2006.01)
*A61M 35/00* (2006.01)
*B65D 47/20* (2006.01)
*A61M 39/22* (2006.01)

(56) References Cited

U.S. PATENT DOCUMENTS

| | | | |
|---|---|---|---|
| 4,596,561 A | 6/1986 | Meyer et al. | |
| 2004/0037613 A1* | 2/2004 | King | 401/183 |
| 2007/0108235 A1* | 5/2007 | Sogaro | 222/209 |

FOREIGN PATENT DOCUMENTS

| | | |
|---|---|---|
| DE | 202006002926 | 4/2006 |
| EP | 0111796 | 6/1984 |
| EP | 0577200 | 1/1994 |
| EP | 1743700 | 1/2007 |
| EP | 1782856 | 5/2007 |
| FR | 714108 | 11/1931 |

OTHER PUBLICATIONS

German Patent Office Search Report as mailed on Jan. 22, 2008 for German Priority Application No. De 20 2007 008 646.6.
Wikipedia Website search results for the word "Schraube" ("Screw"), Jan. 10, 2008, http://de.wikipdeia.org/w/index.php?title=Schraube_%28Verbindungselement%29&oldid=32302865(Eintrag vom May 25, 2007; S.5,Abs.4.

* cited by examiner

APPARATUS FOR DISCHARGING A POURABLE SUBSTANCE

CROSS-REFERENCE TO RELATED APPLICATIONS

This application claims priority to PCT International Application No. PCT/DE2008/001022 filed on Jun. 19, 2008, which claims priority to German Application No. 20 2007 008 646.6 filed on Jun. 20, 2007, incorporated by reference herein.

The invention relates to a device for applying a flowable substance, it comprising an outer shell forming a receptacle for the flowable substance, and at least one insert open at one end and closed at the other end and its shell featuring at least one orifice, the outer shell being shiftable in relation to the insert between a blocked position in which a fluid flow between the outer shell and the insert is blocked by means of a sealing device and an activated position in which the fluid flow between the outer shell and the insert is released.

One such configured applicator device is known from EP 1 782 856 A1. This applicator device comprises a compressible receptacle segment and a duroplastic insert assigned an application tip and which is slidingly guided in the open end of the compressible segment. The insert comprises a transverse channel communicating an axial channel leading to the application tip. The transverse channel or its orifices cooperate with a sealing lip configured at the outer shell so that in a blocked position a fluid flow between the reservoir formed by the outer shell and the transverse channel is blocked and in an activated position the fluid flow is released. Consequently, for activation the insert is shifted in relation to the outer shell so that the transverse channel respectively its orifices negotiate the sealing lip. The offset between the insert and the outer shell respectively the reservoir results from these two components being counterpressurized axially. However, such an axial pressure is difficult to dose.

The invention is based on the object of providing a device of the aforementioned kind in which a defined offset between the cylindrical insert and the outer shell is now achievable by simple ways and means.

This object is achieved in accordance with the invention by the device having the features of claim 1.

The device in accordance with the invention consequently comprises a valve having an insert formed portionally cylindrical, especially forming an inner shell open at one end and closed at the other end and its shell featuring at least one orifice, the outer shell being shiftable in relation to the insert between a blocked position in which a fluid flow between the outer shell and the insert is blocked by means of a sealing device and an activated position in which the fluid flow between the outer shell and the insert is released. To now simply achieve the activated position from the blocked position and vice-versa the insert in accordance with the invention has a male screw thread mating with the outer shell as well as a collar ring acting as a stop for the insert at the outer shell and as an actuator for shifting the outer shell in relation to the insert.

The gist of the invention is consequently to make it possible to set the blocked position or activated position simply by twisting the insert in relation to the outer shell. Twisting can be implemented with high precision and exactly to the angle required simply by manually gripping the collar ring of the insert without risking damage to the components of the valve.

To communicate to the user of the device in accordance with the invention a haptic feeling for when the activated position is attained, the collar ring forms a stop between the insert and the outer shell, defining the activated position. Also feasible is at least one ratchet-locked position between the insert and the outer shell.

In one preferred embodiment of the device in accordance with the invention the outer shell features a female screw thread mating with the male screw thread of the insert, the screw thread always being located downstream of the orifice in the insert. Starting with the blocked position, advancing the insert into the outer shell causes the orifice to negotiate the sealing device so that the fluid flow between the interior of the outer shell and the orifice of the insert is released to the end orifice of the latter.

In an alternative embodiment of the device in accordance with the invention the male screw thread of the insert is self-cutting, it consequently automatically cutting the companion female screw thread in the outer shell when the activated position is implemented.

In another special embodiment of the device in accordance with the invention the sealing device comprises two toroidal sealing lips configured at the inner wall of the outer shell and whose spacing is greater than the maximum dimensions of the orifice in the axial direction of the insert. This ensures the valve is sealed axially on both sides in the blocked position.

In its simplest form the insert of the device in accordance with the invention is configured sleeve- or pot-shaped, its shell wall then featuring the at least one orifice or at least one port.

The outer shell forms a receptacle for a flowable substance which, once the insert is twisted in relation to the outer shell to release the orifice, is able to flow into the insert. The receptacle may come in various shapes and sizes by comprising, for example, a bubble-, tubular-, conical- or beaded-type segment in which the flowable substance is reservoired.

In another aspect of the device in accordance with the invention it may be provided with an automatic reset mechanism so that once opened and after release of the opening force the valve automatically assumes its blocked position.

The device in accordance with the invention is especially suitable for bodily application of pharmaceutical or cosmetic substances to humans or animals, the insert being correspondingly configured as required for the particular application. For example, the insert may feature a pipetting tube or also a brush or miniature sponge. One pharmaceutical substance that can be applied by this device is, for example, a tissue adhesive, a dental adhesive or the like.

The application tip of the insert may be a pipetting tube. To apply a substance reservoired in the outer shell the insert is twisted in relation to the outer shell into the activated position so that the substance can be discharged from the outer shell via the orifices or a transverse channel and an adjoining axial channel and applied by means of the application tip. In this case the outer shell may be formed by a pipetting tube made at least portionally of an elastomeric plastics material so that the flowable substance can be delivered in the activated position to the insert or pipetting tube by applying radial pressure to the outer shell.

In one special embodiment of the device in accordance with the invention the outer shell is engineered as a two-component injection molded part, a first segment of which designed to guide the insert of the outer shell is made of a rigid plastics material and the second segment of which for discharging the flowable substance is made of an elastomeric plastics material.

The cylindrical insert is preferably made of a rigid plastics material, it representing in particular a plastics injection molded part. It is, however, just as feasible that the insert is made of an elastomeric plastics material.

The insert too, may feature a reservoir from which a substance reservoired therein can be discharged via an applicator portion by applying radial pressure to the insert. Such a design makes the device also suitable for application of a two or more component system in which one component is reservoired in the outer shell respectively its receptacle and the second component in the reservoir of the insert. On activating the device by opening the valve designed in accordance with the invention the components can be blended in the reservoir of the insert or also in the receptacle of the outer shell for subsequent application.

The device configured in accordance with the invention for application of a flowable substance is designed especially as a disposable device with the outer shell prefilled. When deactivated, i.e. in the blocked position, the flowable substance is held back in the outer shell by a sealing device, the outer shell then forming a reservoir. This, as a rule, is the state in which the device is furnished. To activate the device all the user has to do is to twist the outer shell in relation to the insert causing it to telescope to make the change from the blocked storage position into the open released position. Activating the device in this way causes the sealing device to negotiate the orifice allowing the flowable substance to flow from the outer shell into the orifice of the insert.

It is also possible to devise the device configured in accordance with the invention for discharging a flowable substance multistaged. In this case the outer shell comprises an axial train of sealing lips, each dimensioned according to the diameter of the orifice, so that the insert acts like a plunger which is successively advanced by screw action into the outer shell. When each sealing lip negotiates the orifice a certain amount of the substance is delivered from the outer shell through the at least one orifice of the insert to its open end for application. It is especially in this way that a calendar-oriented dispenser is achieved which may be correspondingly scaled indicating the precise dispensed amount between the insert and the outer shell to the user.

In another aspect the device in accordance with the invention may also feature a safeguard preventing accidental activation in the form of a pull tab or the like disposed between the insert and the outer shell.

In yet another aspect the outer shell forming the receptacle may also be engineered as an axial train of two chambers separated from each other by a partition, each of the two chambers cooperating with two portionally cylindrical inserts of the aforementioned kind, each assigned an application tip. Each insert is screw thread guided in a corresponding guiding segment of the outer shell for setting between an activated position and a blocked position.

Further benefits and advantageous aspects of the subject matter of the invention read from the description and claims as evident from the drawing.

Two example embodiments of a device in accordance with the invention are evident from the drawing as detailed in the following with reference to the drawing in which.

Shown in the FIGS. 1 to 6 is an applicator device 10 serving, for example, to pipet or apply a flowable substance and comprising an insert 12 and an outer shell 14 representing a receptacle 10 for the flowable substance.

Figure 1:
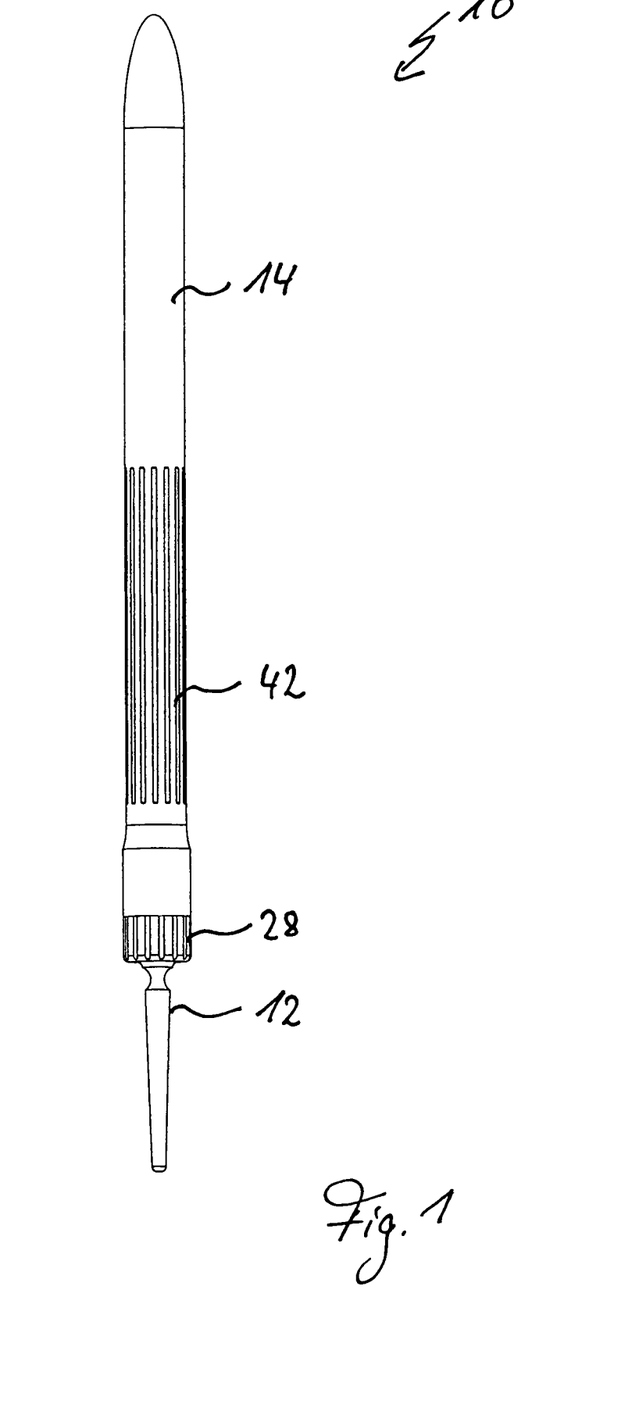
FIG. 1 is a diagrammatic illustration of a pipetting device in accordance with the invention.
Figure 2:
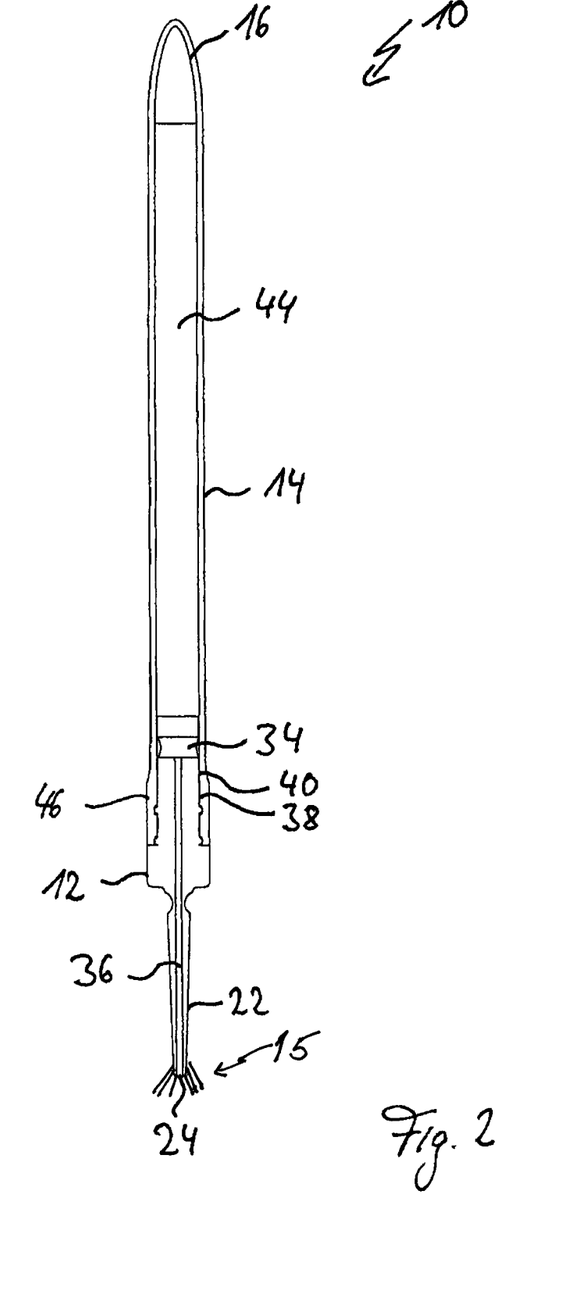
FIG. 2 is a longitudinal section through the pipetting device.
Figure 3:
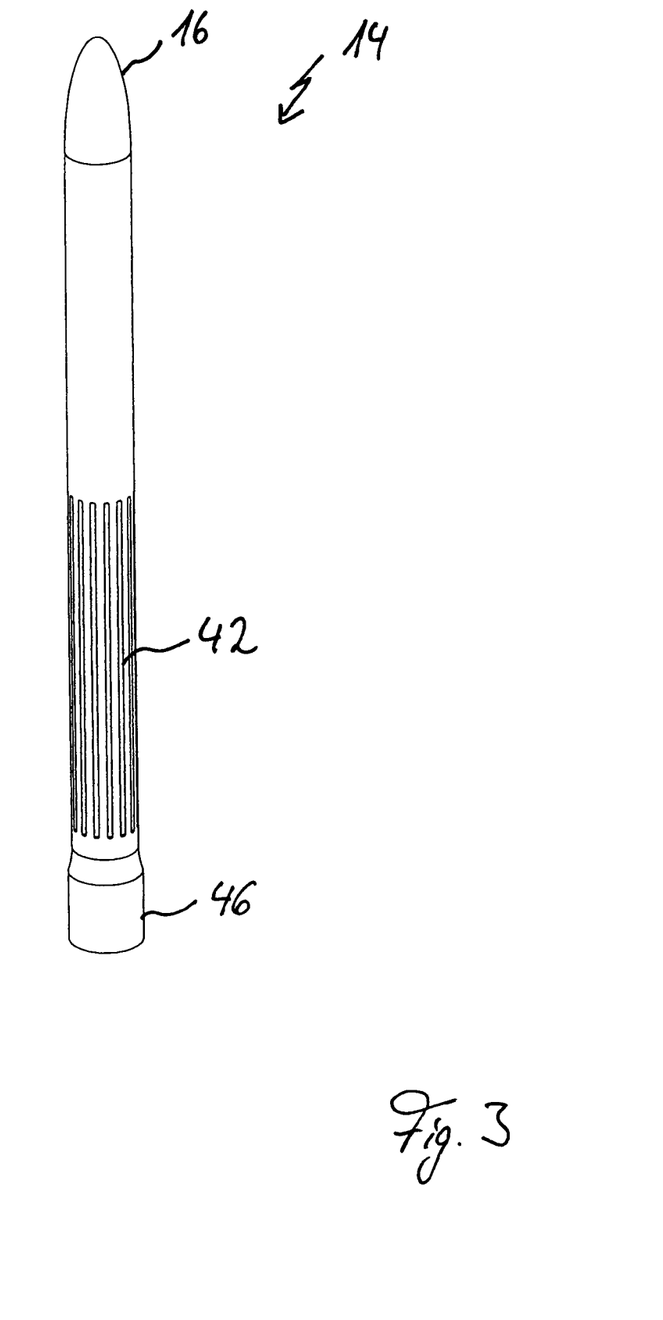
FIG. 3 is a full view of the outer shell of the pipetting device.
Figure 4:
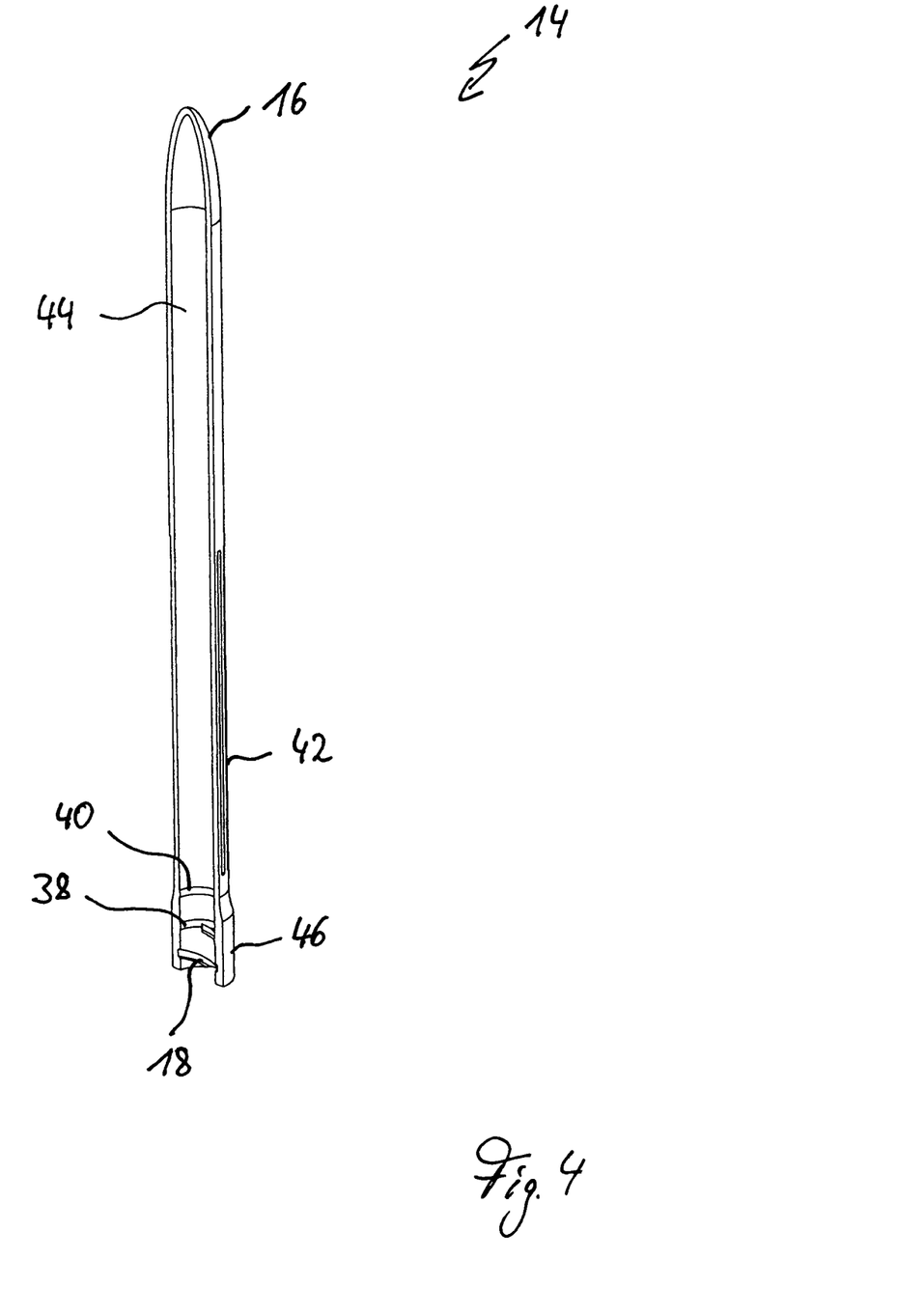
FIG. 4 is a section view of the outer shell.
Figure 5:
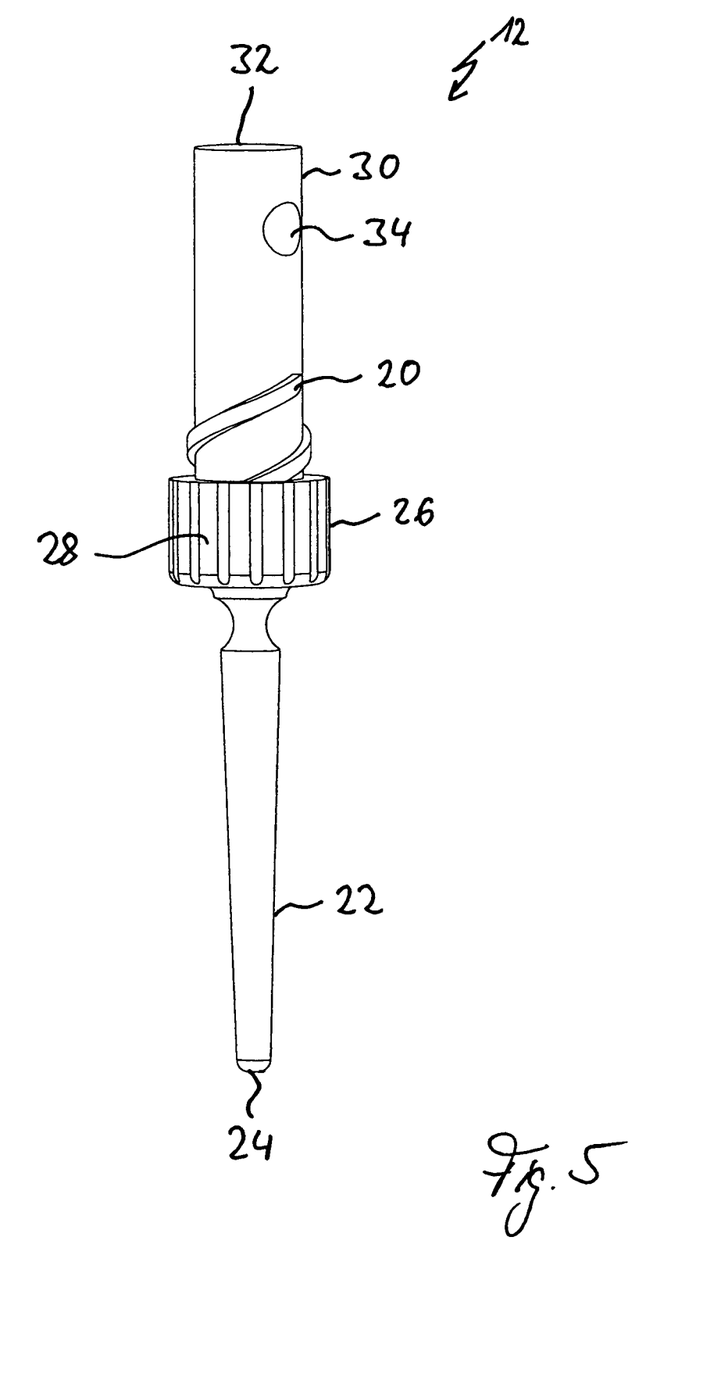
FIG. 5 is a view in perspective of an insert of the pipetting device screwed into the outer shell.
Figure 6:
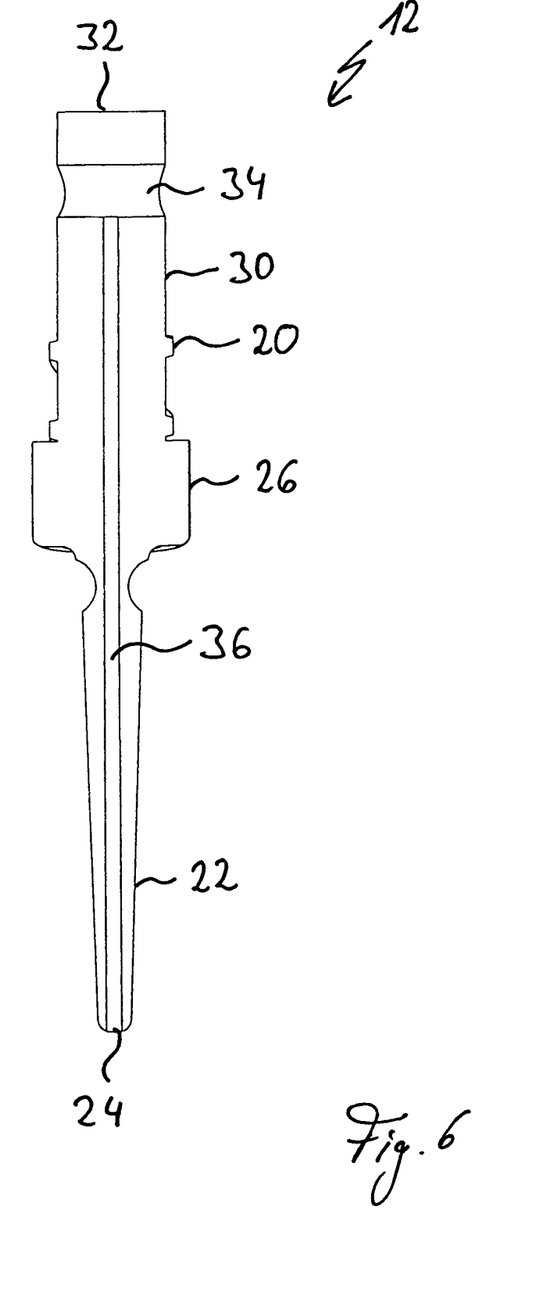
FIG. 6 is a longitudinal section through the insert.

The outer shell 14 shown in a full view in FIG. 2, has a tubular configuration closed off at one end 16. At the opposite end the outer shell 14 is configured open to engage the insert 12.

In a portion adjoining the open end the outer shell 14 has a female screw thread 18 on its inner wall mating with a male screw thread 20 of the insert 12.

The insert 12 comprises a pipetting tip 22 configured as a pipetting tube ending in an application orifice for connecting a brush, flocking 15 or the like for applying the substance to a surface requiring application. At the opposite end of the applicator orifice 24 the pipetting tip 22 is adjoined by a collar ring 26 whose outer shell is engineered fluted 28 extending in the axial direction of the insert 12 and serving to assist gripping the insert 12. The collar ring 26 consequently represents a means for actuating the applicator device 10.

Adjoining in turn the collar ring 26 is a cylindrical or pin-type segment 30 comprising a closed end 32 and provided with a transverse channel 34 forming a transverse orifice. The transverse channel 34 is connected to an axial channel 36 leading to the applicator orifice 24 of the pipetting tip 22.

The cylindrical segment 30 features furthermore adjoining the collar ring 26 the male screw thread 20 mating with the female screw thread of the outer shell 14. In one embodiment of the present invention, the male screw thread 20 is a self-cutting male screw thread.

The outer shell 14 comprises on its inner wall adjoining the female screw thread 18 two sealing lips 38 and 40 protruding radially inwards, whose spacing is slightly larger than the diameter of the transverse channel 34. At its outer surface the outer shell 14 is provided with a fluting 42 to assist gripping.

The outer shell 14 is a two-component injection molded part, it being made of an elastomeric plastics material in the region of its fluting 42 and in a mating portion 46 for the insert 12, i.e. in the portion in which the insert 12 is guided via the male screw thread 20 at the female screw thread 18 of the outer shell 14 and the sealing lips 38 and 40, it being made of a rigid plastics material. Upstream of the elastomeric plastics material portion, i.e. in the portion adjoining the fluting 42 at the end facing away from the insert 12 the outer shell 14 is likewise made of a rigid plastics material.

The insert 12 is injection molded from a rigid plastics material and which can be made of an elastomeric plastics material in the region of the pipetting tip 22. Furthermore, the region of the pipetting tip 22 can be provided flocked for applying the substance reservoired in the outer shell 14.

How the applicator device 10 as shown in the FIGS. 1 to 6 is used will now be described.

The applicator device 10 is furnished with the insert 12 and outer shell 14 in a blocked position, i.e. in a relative position in which although the male screw thread 20 of the insert 12 mates the female screw thread 18 of the outer shell 14, because the transverse channel 34 is disposed between the two sealing lips 38 and 40 at the inner wall of the outer shell 14 any flow of a substance reservoired in the outer shell 14 to the transverse channel 34 and from there via the axial channel 36 to the applicator orifice 24 is blocked.

To activate the device, insert 12 and outer shell 14 are twisted in relation to each other so that the orifices of the transverse channel 34 negotiate the sealing lip 40 and the collar ring 26 is stopped by its portion facing the cylindrical segment 30 at the end of the outer shell 14, the collar ring 26 consequently also forming a stop for the insert 12, in thus producing the activated position. Then, by applying radial pressure to the elastomeric plastics material segment of the outer shell 14 arranged in the region of the fluting 42 the substance reservoired in a receptacle 44 of the outer shell 14 is delivered via the transverse channel 34 and the axial channel 36 to the applicator orifice 24 and applied to a surface requiring application of the substance, for example, of a human body.

Twisting the insert 12 contrary to the twisting direction of the outer shell 14 results in the transverse channel 34 being shifted into the portion disposed between the sealing lips 38 and 40, the applicator device 10 can be simply twisted back to its blocked position. Consequently, the applicator device 10 is a reclosable device.

The connection of the insert 12 to the outer shell 14 also constitutes a safeguard against the insert 12 being accidentally pulled out from the outer shell 14.

Figure 7:
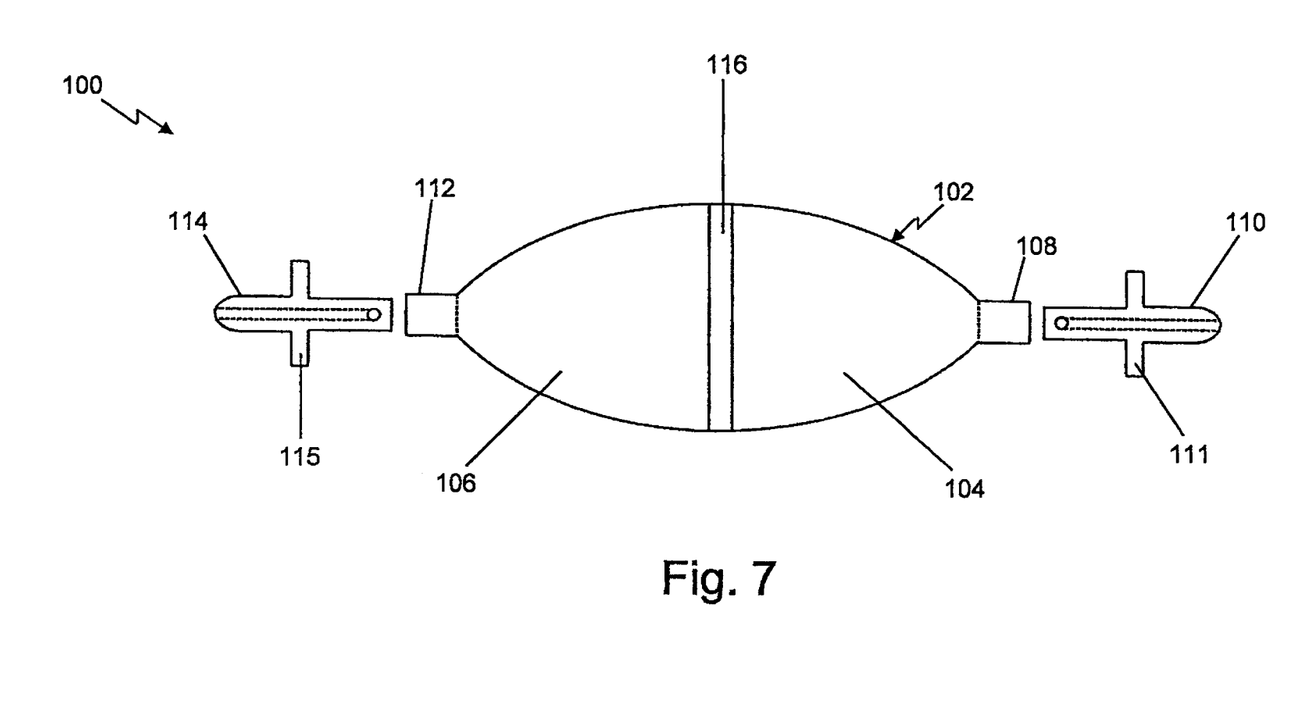
FIG. 7 is a longitudinal section through a second embodiment of a device in accordance with the invention shown dismantled.

Referring now to FIG. 7 there is illustrated an alternative embodiment of a device 100 in accordance with the invention. This device differs from that as described with reference to FIGS. 1 to 6 in that it is designed for application of two components, it having for this purpose a pipetting tube 102 comprising two chambers 104 and 106, each serving to receive a component.

Like the pipetting tube in the embodiment ad in FIGS. 1 to 6 the pipetting tube 102 is configured as a two-component injection molded part, it comprising a first rigid portion 108 for guiding a first insert 110 and a second rigid portion 112 for guiding a second insert 114. The inserts 110 and 114 are configured the same as the insert 12 of the embodiment as shown in FIGS. 1 to 6 and consequently each assigned an application tip. The rigid portions 108 and 112 each made of a rigid plastics material, are each configured the same as the mating portion 46 as shown in FIGS. 1 to 6 in thus each forming a guiding segment for the inserts 110 and 114 each configured as a segment of the outer shell. The inserts 110 and 114 are thus each twistable between a blocked position and an activated position by means of a screw thread relative to the pipetting tube 102, a collar ring 111 and 115 respectively each serving as a stop and actuator.

In the region of the chambers 104 and 106 the pipetting tube 102 is made of an elastomeric plastics material so that the substance reservoired in the corresponding chambers 104 and 106 respectively can be delivered by applying radial pressure in the activated position of each inserts 110 and 114 respectively via the corresponding transverse channel and the corresponding activated position to the application orifice of the corresponding insert and applied to the surface requiring application.

Disposed between the chambers 104 and 106 is a partition 116, likewise made of a rigid plastics material to thus stiffen the pipetting tube 102 in its middle portion.

The inserts 110 and 114 can be flocked in the region of their corresponding application orifice or tip so that the substance concerned can be applied to the surface requiring flocked application.

The functioning of the inserts 110 and 114 in conjunction with the guide segments 108 and 112 of the pipetting tube 102 is the same as that of the insert in the embodiment as shown in FIGS. 1 to 6 engaging the mating segment. In other words, locating the activated position or blocked position is correspondingly achieved by twisting each insert 110 and 114 respectively in relation to the pipetting tube 102.

The invention claimed is:

1. A device for applying a flowable substance, said device comprising:
    an outer shell forming a receptacle for a flowable substance, said outer shell having a first hollow cylindrical segment made of a rigid plastics material and a second hollow cylindrical segment made of an elastomeric plastics material, an end of said first segment being integrally joined to an end of said second segment forming a two-component hollow cylinder defining said receptacle; and
    at least one portionally cylindrical insert having an application tip and being open at one end and closed at another end, said insert further including a shell having at least one orifice connected to the open end, wherein the outer shell is shiftable in relation to the insert between a blocked position, in which a fluid flow of the flowable substance between the outer shell and the insert is blocked by a sealing device, and an activated position, in which the flowable substance flows from the outer shell upon compression of the second segment of the outer shell made of the elastomeric plastic material, into the orifice, and out of the insert open end, wherein the insert has a screw thread mating with the first segment of the outer shell requiring twisting of the insert in relation to the outer shell to move the insert between the blocked position and the activated position, the insert comprising a collar ring acting as a stop for the insert at the outer shell and as an actuator for shifting the outer shell in relation to the insert, said collar ring including a cylindrical gripping surface for grasping by a user to twist the insert relative to the outer shell.

2. The device as set forth in claim 1, in which the screw thread of the insert mates with a female screw thread of the outer shell.

3. The device as set forth in claim 1, in which the screw thread of the insert is a self-cutting male screw thread.

4. The device as set forth in claim 1, in which the stop defines the activated position.

5. The device as set forth in claim 1, in which the sealing device comprises two sealing lips configured on the inner wall of the outer shell and whose spacing is greater than the maximum dimensions of the orifice in the axial direction of the insert.

6. The device as set forth in claim 1, in which the outer shell is a pipetting tube.

7. The device as set forth in claim 1, in which the application tip of the insert is provided flocked.

8. The device as set forth in claim 1, in which the outer shell comprises an axial train of two chambers separated from each other by a partition, each of the two chambers cooperating with two portionally cylindrical inserts, each assigned an application tip.

9. A device for applying a flowable substance, said device comprising
    an outer shell forming a receptacle for a flowable substance, said outer shell having a first hollow cylindrical segment made of a rigid plastics material and a second hollow cylindrical segment made of an elastomeric plastics material, an end of said first segment being integrally joined to an end of said second segment forming a two-component hollow cylinder defining said receptacle and
    at least one cylindrical insert received in said receptacle and including a male screw thread mating with the first segment of the outer shell, said outer shell being twistable along said male screw thread in relation to the at least one cylindrical insert between a blocked position and an activated position, said at least one cylindrical insert further including a collar ring acting as a stop for the at least one cylindrical insert at the outer shell and as an actuator for twisting the outer shell in relation to the at least one cylindrical insert, said collar ring including a cylindrical gripping surface for grasping by a user to twist the outer shell relative to the at least one cylindrical insert; and an application tip assigned to said at least one cylindrical insert, said application tip being open at one end and closed at the other end, and said at least one cylindrical insert including at least one orifice connected to the open end, wherein in said blocked position fluid flow of said flowable substance between the outer shell and the at least one cylindrical insert through said orifice is blocked, and in said activated position, fluid flow of said flowable substance between the outer shell and the at least one cylindrical insert is released through said orifice and out of said open end upon compression of said second segment of the outer shell.

10. The device as set forth in claim 1, in which the cylindrical gripping surface includes fluting extending in an axial direction of the insert.

11. The device as set forth in claim 9 in which the cylindrical gripping surface includes fluting extending in an axial direction of the insert.

12. The device as set forth in claim 1, in which the collar ring acts as a stop for the insert at the outer shell by engaging an end of the outer shell.

13. The device as set forth in claim 9 in which the collar ring acts as a stop for the insert at the outer shell by engaging an end of the outer shell.

\* \* \* \* \*